United States Patent
Garnier

(10) Patent No.: US 6,937,749 B2
(45) Date of Patent: Aug. 30, 2005

(54) PROCESS, SYSTEM, AND KIT FOR EVALUATING THE RELIEF OF THE SKIN WITH A SUBSTRATE

(75) Inventor: Pierre Garnier, Paris (FR)

(73) Assignee: L'Oreal, Paris (FR)

( * ) Notice: Subject to any disclaimer, the term of this patent is extended or adjusted under 35 U.S.C. 154(b) by 83 days.

(21) Appl. No.: 10/270,319

(22) Filed: Oct. 15, 2002

(65) Prior Publication Data

US 2003/0108228 A1 Jun. 12, 2003

Related U.S. Application Data

(63) Continuation of application No. PCT/FR02/00730, filed on Feb. 28, 2002.
(60) Provisional application No. 60/387,369, filed on Jun. 11, 2002.

(30) Foreign Application Priority Data

Mar. 2, 2001 (FR) .............................. 01 02888

(51) Int. Cl.⁷ .............................................. G06K 9/00
(52) U.S. Cl. ...................... 382/128; 600/306; 600/476
(58) Field of Search .......................... 382/100, 108, 382/128; 348/77; 600/306, 476, 477; 356/600; 264/222, DIG. 30; 425/2; 118/31.5; 427/1

(56) References Cited

U.S. PATENT DOCUMENTS

| | | | |
|---|---|---|---|
| 3,029,538 A | * 4/1962 | Terek et al. ................. | 41/26 |
| 3,571,947 A | * 3/1971 | Maddison et al. ............. | 35/17 |
| 3,965,888 A | 6/1976 | Bender ....................... | 128/2 W |
| 4,313,393 A | 2/1982 | Barbuscio et al. ............. | 116/200 |
| 5,088,502 A | 2/1992 | Miller ....................... | 128/759 |
| 5,211,894 A | 5/1993 | Groh et al. ................. | 264/40.1 |
| 5,343,536 A | * 8/1994 | Groh ......................... | 382/6 |
| 5,684,573 A | 11/1997 | Khazaka et al. .............. | 356/36 |
| 6,571,003 B1 | * 5/2003 | Hillebrand et al. .......... | 382/118 |
| 2002/0065456 A1 | * 5/2002 | Bazin et al. ................ | 600/407 |
| 2002/0090123 A1 | * 7/2002 | Bazin ........................ | 362/128 |
| 2002/0182149 A1 | 12/2002 | Telesca et al. .............. | 424/9.1 |
| 2002/0182235 A1 | 12/2002 | Slavtcheff et al. .......... | 424/401 |

FOREIGN PATENT DOCUMENTS

| | | | |
|---|---|---|---|
| FR | 2063743 A1 | 7/1971 | ........... A61B/10/00 |
| FR | 2 658 713 A | 8/1991 | ........... A61B/5/117 |
| FR | 2 774 287 A | 8/1999 | ........... A61K/7/50 |
| JP | 11-309132 A | 11/1999 | ........... A61B/5/107 |
| WO | WO 02/096291 A1 | 12/2002 | ........... A61B/5/103 |
| WO | WO 02/096292 A1 | 12/2002 | ........... A61B/5/103 |

OTHER PUBLICATIONS

Copy of Packaging (external box and enclosed internal printed matter)—Pond's Dramatic Results—Advanced Anti–Aging Care—Anti–Wrinkle Cream; introduction date believed to be Mar. 2002.
Copy of Packaging (external box and enclosed internal printed matter)—Pond's Dramatic Results—Advanced Anti–Aging Care—Active Face & Neck Moisturizer; introduction date believed to be Mar. 2002.

* cited by examiner

*Primary Examiner*—Andrew W. Johns
(74) *Attorney, Agent, or Firm*—Oblon, Spivak, McClelland, Maier & Neustadt, P.C.

(57) ABSTRACT

A process, system, and kit for evaluating the relief of the skin using a substrate with an adhesive surface. The process includes the steps of applying the substrate onto a test zone of the skin so that the adhesive surface is in contact with the skin at contact locations; removing the substrate; and evaluating the image formed on the adhesive surface. The image results from the modification of the adhesive surface at the contact locations. In a preferred embodiment, the adhesive surface, when applied to the skin, is not in appreciable contact with the sunken zones of the skin, such as the wrinkles or lines.

39 Claims, 2 Drawing Sheets

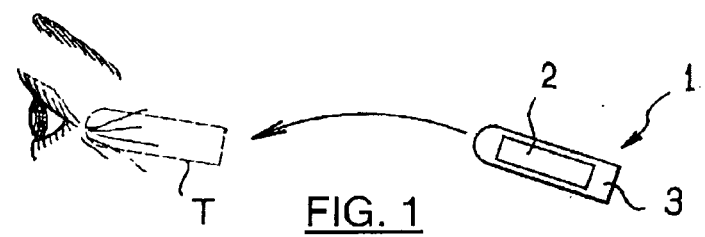
FIG. 1
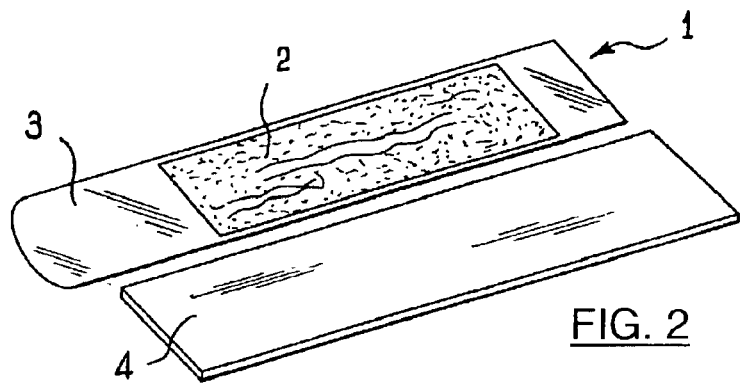
FIG. 2
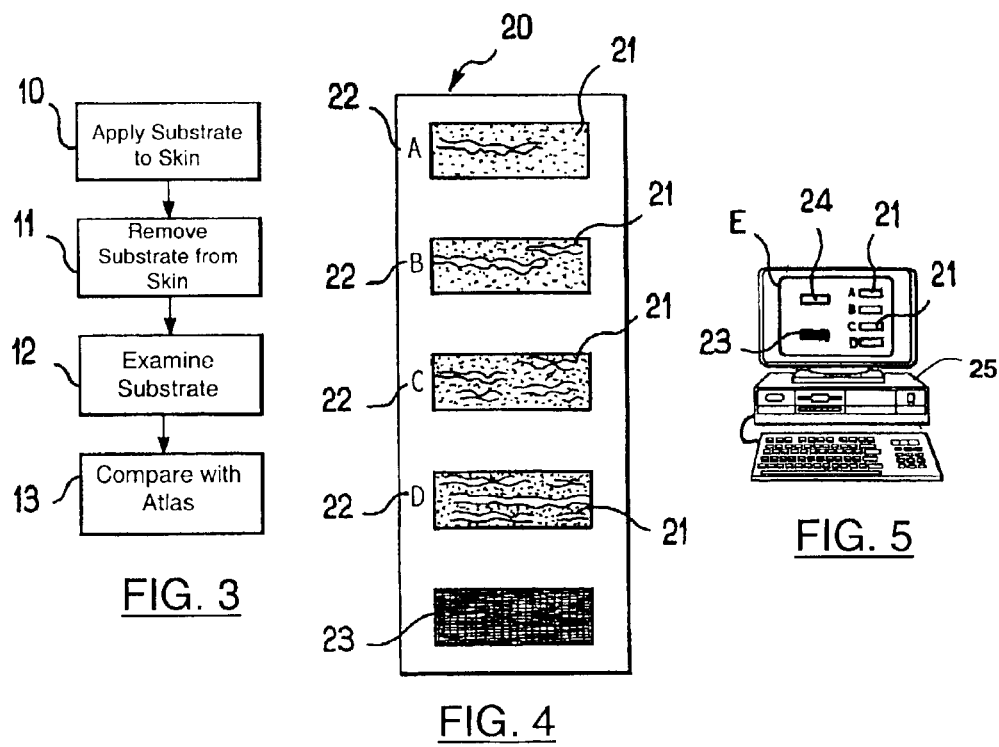
FIG. 3
FIG. 4
FIG. 5

PROCESS, SYSTEM, AND KIT FOR EVALUATING THE RELIEF OF THE SKIN WITH A SUBSTRATE

CROSS REFERENCE TO RELATED APPLICATIONS

This document is a continuation of PCT application number PCT/FR02/00730, filed Feb. 28, 2002, and claims priority under 35 U.S.C. §120 to the same; and to provisional application No. 60/387,369, filed Jun. 11, 2002 under 35 U.S.C. §119(e); and to French application number 01 02888, filed Mar. 2, 2001 under 35 U.S.C. §119; the entire contents of these prior applications are hereby incorporated by reference.

BACKGROUND OF THE INVENTION

1. Field of the Invention

The present invention relates to a process, system, and kit for evaluating the relief of the skin.

2. Description of the Background

To visualize the signs of aging of the skin, a skin print can be made using a silicone-containing malleable compound, such as the compound sold under the trade name Silflow™. This conventional process, however, can be relatively tricky and costly to operate because it requires the use of a relatively complex measuring instrument, which necessitates the presence of specially trained personnel skilled in taking prints. This process is not suitable for operation by the consumers themselves or for walk-in customers, for example at a sales outlet.

It is also known to determine the degree of dryness of the skin by sampling corneocytes from the stratum corneum using an adhesive substrate, such as the substrate described in U.S. Pat. No. 5,088,502 and sold by the Cuderm Corporation under the registered trademark D-Squame™.

SUMMARY OF THE INVENTION

A need exists to evaluate the relief of the skin, especially its state of aging, in a manner that is simple and inexpensive while nevertheless being sufficiently precise. The present invention meets this need by virtue of a new process, system, and kit. The process can include applying a substrate with an adhesive surface onto a test zone of the skin so that the adhesive surface is in contact with the skin at contact locations. Thereafter, the substrate is removed and the image formed on the adhesive surface can be evaluated. The image results from the modification of the adhesive surface at the contact locations. In a preferred embodiment, the adhesive surface, when applied to the skin, is not in appreciable contact with the sunken zones of the skin, such as the wrinkles or lines.

The applicant has discovered that the use of a substrate with an adhesive surface, surprisingly allows visualization of the relief and the signs of aging, in particular the lines and wrinkles present at the surface of the skin, by making a two-dimensional print of the surface of the skin. The adhesive substrate can be, for example, one as described in U.S. Pat. No. 5,088,502. The adhesive substrate, by sticking to the "plateaus" of the skin, acts in the manner of an inkpad and allows the reconstitution of the condition of the surface as a negative. The modification of the appearance of the adhesive surface can result from the presence on its surface of particles stripped from the skin, for example of dead cells or other impurities, and can also result from the deposition of particles of adhesive on the skin where the adhesive surface adhered to the skin.

The adhesive substrate used can be transparent. The examination of the adhesive substrate can be accomplished by placing it in front of a background of dark color. In a preferred embodiment, the adhesive substrate can be placed on the background of dark color without allowing it to adhere thereto.

Advantageously, the substrate can have a gripping tab extending from at least one side of the adhesive surface. The test zone can be chosen from among regions of the skin including, but not limited to, the crow's foot region, the forehead, and the corner of the mouth.

In one embodiment of the invention, the image formed on the adhesive surface is compared with reference images. For example, the reference images can correspond to various degrees of aging of the skin, in order to deduce therefrom the degree of aging of the skin of the person being tested. These reference images may be printed, electronically stored, and/or displayed on the monitor of a computer. The comparison between the image formed on the substrate and the reference images can be performed with the naked eye. Alternatively or additionally, the comparison between the image formed on the substrate and the reference images can be performed by automated techniques, such as using computer hardware and software.

The image formed on the adhesive surface of the substrate can be analyzed remotely. In other words, the skin can be imaged with the substrate in one location, the image can then be sent to another location and analyzed in that other location. In one embodiment, the image can be digitized, transmitted, then remotely analyzed. For example, the digitized image can be transmitted in the form of an electronic file.

It is possible to process the image formed on the adhesive surface for the purpose of determining characteristic parameters of the test zone. Such processing can include counting the wrinkles or lines, and/or measuring their dimensions and their orientation.

In one embodiment of the invention, images are formed on different substrates applied successively to the test zone. These images can then be compared in order, for example, to demonstrate the effect of a treatment or the need for a treatment. The formed images can be recorded, for example electronically. The recorded images can be displayed simultaneously to allow a person to appreciate the effects of a treatment or to become aware of the need for a treatment.

Another object of the invention is an information-processing system. In one embodiment, the system is an Internet server. The system can be configured to (a) receive digital images, and (b) analyze the digital images. Each of the images can correspond to the modification of the appearance of an adhesive surface that has been applied onto the skin where the adhesive surface was in effective contact with the skin. In a preferred embodiment, the adhesive surface was not in appreciable contact with the sunken zones of the skin, such as the wrinkles or lines.

Advantageously, the information-processing system can be configured to determine, after analysis of an image, the degree of aging of the corresponding skin. This information-processing system can also be configured to:

a) establish a diagnosis based on the analysis of each received image, and b) on the basis of this diagnosis, select an appropriate care product from among a predetermined set of products.

The information-processing system can also be configured to send the result of the analysis, and/or a suggestion for a care or cosmetic product, and/or a prescription for a care or cosmetic product. In a preferred embodiment, the system sends this information to the person who has transmitted an image. The system can send this information via regular mail, e-mail, telephone, or other information transmission mechanism.

Yet another object of the invention is a cosmetic treatment process including applying a substrate provided with an adhesive surface onto a test zone of the skin. Thereafter, the substrate is removed and the image formed on the adhesive surface of the substrate can be analyzed. This image results from the modification of the appearance of the adhesive surface where the adhesive surface was in effective contact with the skin, the adhesive surface not having been in appreciable contact with the sunken zones of the skin, such as the wrinkles or lines. The process can also include a step of recommending a care product in view of this diagnosis, and applying the recommended product on the skin.

Another object of the invention is a process for determining the efficacy of a cosmetic or care product, for example an anti-wrinkle product. The process can include applying a substrate with an adhesive surface onto a test zone of the skin. Thereafter, the substrate is removed and a product having an action on the wrinkles is applied on the test zone. A new substrate with an adhesive surface can then be applied onto the test zone. This new substrate is removed and the images formed on the substrates before and after application of the product are compared in order to deduce useful information about the efficacy of the product. Each image can result from the modification of the appearance of the adhesive surface, such a modification occurring where the adhesive surface was in effective contact with the skin, the adhesive surface not having been in appreciable contact with the sunken zones of the skin, such as the wrinkles or lines.

Another object of the invention is an atlas with which the relief of the skin can be evaluated. The atlas includes a plurality of reference images, each representative of the image formed on a substrate provided with an adhesive zone, after application on a test zone of the skin. These images can have patterns, for example lines or points indicative of the presence of wrinkles, lines or pores on the test zone and corresponding, for example, to different degrees of aging of the skin.

Another object of the invention is a kit including (a) a skin-treatment product, for example an anti-wrinkle product, (b) at least one substrate with an adhesive surface configured to be applied onto a test zone of the skin, and (c) an atlas that permits, by comparison with the image formed on the adhesive surface of the substrate, evaluation of the relief of the skin, for example its degree of aging.

BRIEF DESCRIPTION OF THE DRAWINGS

A more complete appreciation of the invention and many of the attendant advantages thereof will be readily obtained as the same becomes better understood by reference to the following detailed description when considered in conjunction with the accompanying drawings, in which:

FIG. 1 shows the application of a substrate onto a test zone situated at the crow's foot region, FIG. 2 illustrates the substrate after removal from the skin and before being placed in front of a dark background in order to reveal the modification in appearance of the adhesive surface, FIG. 3 is a flow chart illustrating different steps of a process according to an embodiment of the invention, FIG. 4 illustrates an atlas permitting comparison of the image formed on the substrate with reference images, FIG. 5 shows an information-processing system displaying an atlas permitting comparison of the image formed on the substrate with reference images.

DETAILED DESCRIPTION OF THE PREFERRED EMBODIMENTS

Figure 6:
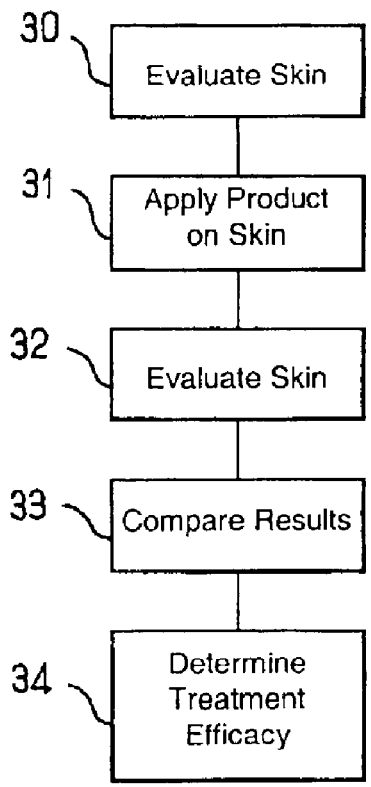
FIGS. 6 to 8 are flow charts illustrating different processes according to various embodiments of the invention.

FIG. 1 illustrates an adhesive substrate 1 with an adhesive surface 2 and a non-adhesive tab 3. The adhesive substrate 1 can be gripped with non-adhesive tab 3 so that the fingers do not come into contact with adhesive surface 2. The adhesive composing adhesive surface 2 is, for example, a solid adhesive, and can be applied in the form of a fixed layer of substantially uniform thickness. Substrate 1 can be, for example, a substrate made by the Cuderm Corporation under the registered trademark D-Squame™. As shown in FIG. 1, the substrate 1 can be transparent. Non-transparent substrate can also be used. The substrate 1 can be coated with a removable protective film, not shown, which covers adhesive surface 2 before use.

The substrate 1 can be applied onto the skin without excessive pressure, on a test zone T. The test zone T can be situated, for example, in the crow's foot region, as shown in FIG. 1. The test zone T can be treated beforehand with a care product or a cosmetic product, such as a makeup remover and a cleaner.

Particles present on the surface of the skin and situated at the level of the "plateaus," such as dead cells, can adhere to the adhesive surface 2, whereas particles situated in the sunken zones formed between the "plateaus" by the wrinkles or lines do not come into effective contact with the adhesive surface 2. As a result, when the substrate 1 is removed, the adhesive surface 2 forms a negative image, which reveals the wrinkles or lines present on test zone T. Adhesive particles can also remain on the skin at the level of the "plateaus," thus contributing to the modification in appearance of the adhesive surface.

To highlight the image formed on the adhesive surface 2, the substrate 1 can be placed in front of an opaque background 4 of dark color, e.g., black.

FIG. 3 summarizes different steps performed when using the substrate 1 in a preferred embodiment. At step 10, the substrate 1 is applied onto the skin. At step 11, the substrate 1 is removed and at step 12, the substrate is examined visually. Advantageously, this examination can include, at step 13, a comparison during which the image formed on the substrate is compared with reference images of an atlas 20 or a comparison scale, such as the one illustrated in FIG. 4.

Images 21 can correspond to different degrees of aging of the skin. For example, one of the images 21 can be an image that would be obtained on the substrate 1 by applying it onto the crow's foot region of a person with young skin. The other images 21 can correspond to the images that would be obtained after application of the substrates 1 on skins having increasingly greater degrees of aging. Preferably, as shown in FIG. 4, the atlas can be provided with an alphanumeric code opposite each reference image 21. For example, the letter A can correspond to the absence of pronounced signs of aging, while the letter D can correspond to the greatest degree of aging, the images 21 identified by letters B and C corresponding to intermediate degrees.

The atlas 20 can be composed of prints, photos, or scans of used substrates or can be composed of drawn images or computer generated images. The reference images of the atlas 20 can be printed, stored, and/or displayed on a monitor E of a computer 25, as illustrated in FIG. 5. Advantageously, the atlas 20 can be provided with a dark zone 23, in front of which substrate 1 can be placed after application on the skin. The dark zone 23 can highlight the modification in appearance of the adhesive surface 2. When the monitor E is used, the images 21 can be displayed simultaneously with a dark zone 23, in front of which the substrate 1 is placed. Alternatively, the substrate 1 can be positioned at a predetermined place 24 of the monitor E, where there are successively displayed images configured to permit the observer to determine the degree of aging of the skin by observing the monitor E through the substrate 1.

In another embodiment, the image formed on the substrate 1 can be displayed by the monitor E. In this embodiment, the reference images of the atlas 20 are electronically stored in a storage device (e.g., a ROM, a RAM, a hard drive, a floppy disk, CD ROM, or other electronic storage medium) in a computer, such as computer 25. The computer 25 can include a receiver (not shown), such as a modem or other network interface, configured to receive images from a user. The user can be, for example, a person being tested, a person working for a skin product business, or a skin technician. The user can send images formed on the adhesive surface 2 to the receiver via a network (not shown), such as the Internet.

The computer 25 can also include an analyzer (not shown) configured to analyze the images received by the receiver. For example, the analyzer can compare the images received from the receiver to reference images stored in the storage device of the computer 5. The computer 5 can also include a result output (not sown), such as a modem or other network interface, configured to send the results generated by the analyzer to the user. The result output can send the results via a network (not shown), which can be the same network used to send the images from the user.

In this embodiment, the user can, for example, e-mail an image of the adhesive surface 2 to the computer 5 and receive back from the computer 5 an e-mail with a diagnosis, prescription, and/or treatment recommendations. In this embodiment, the computer 5 functions as a diagnostic center and as an information processing system. The analyzer and its interaction with the receiver, storage device and result output can be implemented using a conventional general purpose microprocessor(s) programmed according to the teachings of the present specification, as will be appreciated to those skilled in the relevant arts. Appropriate software coding can readily be prepared by skilled programmers based on the teachings of the present disclosure, as will also be apparent to those skilled in the relevant arts.

FIG. 6 summarizes different steps of a process with which the efficacy of a treatment can be determined according to one embodiment of the present invention. At step 30, a first evaluation of the skin is performed. For example, the process described with reference to FIG. 3 can be performed at step 30. At step 31, a product is applied. The product can be, for example, an anti-wrinkle product, which has an action on the wrinkles or lines present in the test zone on which the substrate 1 is applied.

After one or more applications of the product, another evaluation of the test zone is performed at step 32. This second evaluation can be performed in the same manner as the first evaluation, with a new substrate 1. This second evaluation can be performed by performing the process of FIG. 3. At step 33, the results of the different evaluations are compared, and at step 34, the efficacy of the treatment is determined. Advantageously, the process of FIG. 6 can be used by the consumer himself or by a professional in a specialized center or at a sales outlet, for example.

Figure 7:
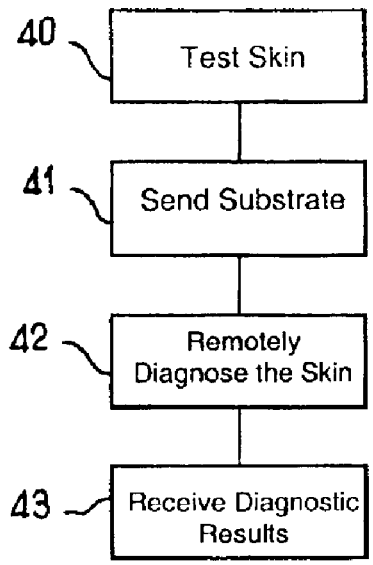

The image formed on the substrate can be analyzed remotely, for example in the manner illustrated in FIG. 7. At step 40, the skin is tested, for example by applying the adhesive substrate 1 to a test zone of the skin and removing the substrate 1. At step 41, the adhesive substrate 1 is sent to a diagnostic center which, at step 42, remotely establishes a diagnosis. At step 43, the person being tested can receive the result of the analysis from the diagnostic center, which can include a diagnostic, and/or instructions for skin care, and/or a prescription for a product, such as an anti-wrinkle product.

Figure 8:
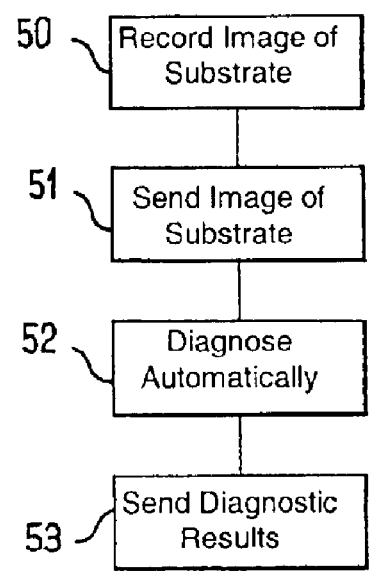

In another embodiment shown in FIG. 8, at step 50, the image formed on substrate 1 can be recorded and stored. For example, the image formed on the substrate 1 can be recorded with a camera or a scanner and stored in a computer memory. At step 51, the image can be sent to a diagnostic center, which can be for example computer 25 shown in FIG. 5. In a preferred embodiment, the image is sent electronically to an Internet site. Other transmission mechanisms to the diagnostic center are possible, for example via regular mail, facsimile, or electronic mails. The diagnosis center can established a diagnostic at step 52. In a preferred embodiment, the diagnostic is performed automatically, for example by performing an automatic comparison of images with a shape-recognition engine. The diagnostic center can perform other functions, such as prescribing a product for treating the skin, and/or providing instructions on how to care for the skin. At step 53, the diagnostic center transmits information (e.g., the diagnostic, a prescription, other information). In a preferred embodiment, the diagnostic center transmits the information to the person being tested. Other destinations are possible, for example, the diagnostic center can send the information to a sales outlet, such as where the person being tested shops, or to a skilled technician, such as a dermatologist. The diagnostic center can transmit this information by conventional mail, by telephone, by facsimile, or by electronic mail.

The Internet server to which the images are sent can be configured to store all the images received. The Internet server can display these images simultaneously or successively. The Internet server can compare the images to determine the efficacy of a treatment or to decide on the need for a treatment, for example.

Figure 9:
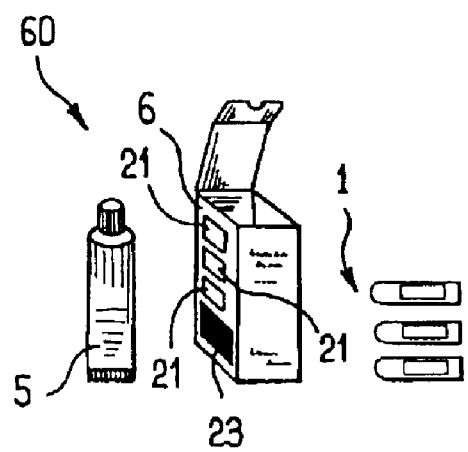
FIG. 9 illustrates a kit including a product container, a plurality of adhesive substrates and a package on which there are printed reference images.

As shown in FIG. 9, one or more substrates can be sold with a skin product enclosed in a container 5 and its package 6 in the form of a kit. The substrates 1 and the container 5 are adapted to fit inside the package 6. The product can be, for example, an anti-wrinkle product. In this embodiment, the package 6 can include a set of reference images 21 so as to provide a self-evaluation atlas. The package 6 can also include a dark zone 23 to facilitate observation of the image formed on adhesive substrate 1. The references images 21 can be displayed on an outside surface of the package 6 (as shown in FIG. 9), or can be printed on a support that fits inside the package 6. For example, the support can be made of paper, cardboard, plastic, or another media.

Figure 10:
FIG. 10 illustrates a substrate having an adhesive surface of circular contour.

Of course, the invention is not limited to the examples given in the foregoing. In particular, the substrate 1 can be implemented in multiple forms. For example, the adhesive surface 2 can have a circular contour, as illustrated in FIG. 10. The substrate 1 can be nontransparent and of dark color, for example, in order to obviate the need for placing it in front of a dark zone.

Although the invention has been described mainly as regards its application to the evaluation of reliefs of the skin such as wrinkles or lines, the invention is also applicable to the evaluation of reliefs of the skin such as pores, scars, lines of the palm and fingerprints.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters Patent of the United States is:

1. A process for evaluating skin relief, comprising:
    applying a substrate with an adhesive surface onto a test zone of a skin so that the adhesive surface is in contact with the skin at contact locations and not in contact with sunken zones of the skin;
    removing the substrate; and
    evaluating an image formed on the adhesive surface of the substrate by comparing said image to at least one reference image, wherein said image results from the modification of an appearance of the adhesive surface at said contact locations.

2. A process according to claim 1, further comprising the step of evaluating a degree of aging of the skin based on said image.

3. A process according to claim 1, wherein said substrate is transparent.

4. A process according to claim 1, wherein said substrate comprises a gripping tab extending from at least one side of the adhesive surface.

5. A process according to claim 1, wherein said test zone is selected from the group consisting of a crow's foot region, a forehead, and a corner of a mouth.

6. A process according to claim 1, further comprising the step of comparing said image formed on the adhesive surface to several reference images.

7. A process according to claim 6, wherein said reference images correspond to different degrees of aging of the skin.

8. A process according to claim 6, wherein the reference images are printed.

9. A process according to claim 6, wherein the reference images are stored in a computer.

10. A process according to claim 6, wherein the reference images are displayed on a computer monitor.

11. A process according to claim 6, wherein said comparing step is performed with the naked eye.

12. A process according to claim 6, wherein said comparing step is performed by automated techniques.

13. A process according to claim 1, further comprising the step of sending said image to a remote location.

14. A process according to claim 13, wherein said evaluating step is performed at said remote location.

15. A process according to claim 1, further comprising the step of digitizing said image.

16. A process according to claim 15, further comprising the step of transmitting said digitized image to a remote location.

17. A process according to claim 16, wherein said evaluating step is performed at said remote location.

18. A process according to claim 16, wherein said transmitting is performed over the Internet.

19. A process according to claim 17, wherein said evaluating step comprises determining characteristic parameters of the test zone.

20. A process according to claim 1, further comprising applying and removing successively a plurality of substrates on said test zone thereby forming a plurality of successive images.

21. A process according to claim 20, further comprising the step of recording said plurality of images.

22. A process according to claim 21, further comprising the step of comparing said recorded images.

23. A process according to claim 21, further comprising the step of analyzing an effect of a treatment performed between successive images.

24. A process according to claim 21, further comprising the step of determining a need for a skin treatment.

25. A process according to claim 22, further comprising the step of simultaneously displaying said plurality of images so as to allow a person to perform said comparing step.

26. A process according to claim 22, wherein said comparing step is performed by a computer.

27. A process according to claim 1, wherein said image represents winkles present in said test zone.

28. A process according to claim 1, wherein said image represents lines present in said test zone.

29. A process according to claim 1, further comprising evaluating a degree of aging of the skin based on said image.

30. A process for determining an efficacy of a product, comprising:
    applying a first substrate with a first adhesive surface onto a test zone of the skin;
    removing the first substrate;
    applying a product on the test zone;
    applying a second substrate with a second adhesive surface onto the test zone;
    removing said second substrate;
    comparing a first image formed on the first substrate before application of the product to a second image formed on the second substrate after application of the product thereby deducing information about the efficacy of the product.

31. A process according to claim 30, wherein:
    said applying steps are performed so that the first and second adhesive surfaces are in contact with the skin at contact locations and not in contact with sunken zones of the skin, and
    said first and second images result from a modification of an appearance of the adhesive surfaces at the contact locations.

32. A process according to claim 30, wherein said product has an effect on wrinkles and said comparing step provides information about the efficacy of said product on wrinkles.

33. A process for evaluating skin relief, comprising:
    applying a substrate with an adhesive surface onto a test zone of a skin so that the adhesive surface is in contact with the skin at contact locations and not in contact with sunken zones of the skin;
    removing the substrate;
    placing said substrate in front of a background of dark color; and then
    evaluating an image formed on the adhesive surface of the substrate, wherein the image results from the modification of an appearance of the adhesive surface at said contact locations.

34. A process according to claim 33, wherein the placing said substrate in front of said background of dark color is performed without making said substrate adhere to said background of dark color.

35. A process according to claim 33, wherein said substrate is transparent.

36. A process according to claim 33, wherein said substrate comprises a gripping tab extending from at least one side of the adhesive surface.

37. A process according to claim 33, further comprising comparing said image formed the adhesive surface to reference images.

38. A process according to claim 37, wherein said comparing is performed with the naked eye.

39. A process according to claim 33, wherein said image represents wrinkles present in said test zone.

* * * * *